United States Patent

Khouri et al.

Patent Number: 5,142,049
Date of Patent: Aug. 25, 1992

[54] ORTHO ESTER-SUBSTITUTED CHLOROTRIAZINES AS CAPPING AGENTS FOR POLYPHENYLENE ETHERS

[75] Inventors: Farid F. Khouri, Clifton Park; John T. Jackman, Schenectady; Otto Phanstiel, IV, Clifton Park, all of N.Y.

[73] Assignee: General Electric Company, Schenectady, N.Y.

[21] Appl. No.: 567,574

[22] Filed: Aug. 15, 1990

[51] Int. Cl.⁵ .............................. C07D 251/26
[52] U.S. Cl. .................................... 544/218
[58] Field of Search ........................ 544/218

[56] References Cited

U.S. PATENT DOCUMENTS

| | | | |
|---|---|---|---|
| 4,284,772 | 8/1981 | Hoentjen et al. | 544/218 |
| 4,407,748 | 10/1983 | Gorbacheva et al. | 544/218 |
| 4,931,087 | 6/1990 | Shigematsu et al. | 544/218 |
| 5,006,155 | 4/1991 | Rheinheimer et al. | 544/218 |

Primary Examiner—John M. Ford
Attorney, Agent, or Firm—William H. Pittman; James C. Davis, Jr.

[57] ABSTRACT

Ortho ester-substituted chlorotriazines are prepared by the reaction of a dichlorotriazine with a reactive compound containing an ortho ester group, preferably a 4-(2-methoxy-2-methyl-1,3-dioxolan-4-yl)methyl group. They are useful as capping agents for polyphenylene ethers. The capped polyphenylene ethers form copolymer-containing compositions with polyesters, polyamides and other polymers containing carboxylic acid or amine groups.

14 Claims, No Drawings

ORTHO ESTER-SUBSTITUTED CHLOROTRIAZINES AS CAPPING AGENTS FOR POLYPHENYLENE ETHERS

This invention relates to reagents useful for reactively capping polyphenylene ethers.

The polyphenylene ethers are a widely used class of thermoplastic engineering resins characterized by excellent hydrolytic stability, dimensional stability, toughness, heat resistance and dielectric properties. However, they are deficient in certain other properties such as workability and solvent resistance. Therefore, there is a continuing search for means for modifying polyphenylene ethers to improve these other properties.

Among the means being studied are blending of polyphenylene ethers with certain other resinous materials such as polyesters, polyamides or olefin polymers. Blends of these other materials with polyphenylene ethers are, however, usually incompatible. Molded parts fabricated from such blends are generally brittle and may undergo catastrophic delamination upon impact.

Compatibilization of blends of polyphenylene ethers with these other polymers may be achieved by several methods. A frequently preferred method is the formation of a copolymer of the polyphenylene ether with the other polymer; when present in the blend, said copolymer serves as a compatibilizer for the uncopolymerized constituents.

One method for preparing copolymers of polyphenylene ethers with polyesters, polyamides and the like is disclosed in copending, commonly owned application Ser. No. 07/351,905. This method comprises capping the polyphenylene ether by reaction with an epoxychlorotriazine such as 2-chloro-4,6-diglycidoxy-1,3,5-triazine, 2-chloro-4-(n-butoxy)-6-glycidoxy-1,3,5-triazine or 2-chloro-4-(2,4,6-trimethylphenoxy)-6-glycidoxy-1,3,5-triazine. Such capped polyphenylene ethers readily form copolymers with nucleophilic polymers such as polyesters, polyamides and functionalized olefin polymers, and blends containing such copolymers have numerous desirable properties including high impact and tensile strengths and structural integrity.

However, the use of epoxychlorotriazines as capping agents has certain disadvantages. Among these are the necessity to use compounds such as glycidol in the preparation of the epoxychlorotriazines. Glycidol is expensive, and also has carcinogenic properties. Interest continues, therefore, in the development of new capping reagents capable of forming polyphenylene ethers which are reactive with other polymers.

The present invention includes a class of compounds capable of reaction with polyphenylene ethers to form capped polymers which are capable of forming copolymer-containing blends with polymers which are otherwise incompatible with polyphenylene ethers.

In one of its aspects, the invention includes ortho ester-substituted chlorotriazines of the formula

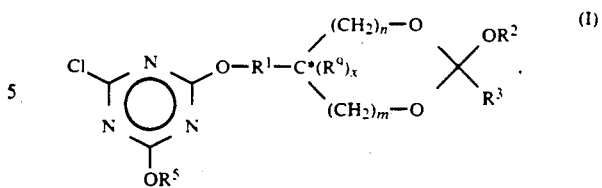

wherein:

$R^1$ is a $C_{1-6}$ alkylene radical;

$R^2$ is a $C_{1-4}$ primary or secondary alkyl radical or is an alkylene radical forming a second 5- or 6-membered ring with $C^*$, and $R^3$ is a $C_{1-4}$ primary or secondary alkyl or $C_{6-10}$ aromatic radical, or $R^2$ and $R^3$ together with the atoms connecting them form a 5-, 6- or 7-membered ring;

$R^5$ is an alkyl, cycloalkyl or aromatic radical or a radical of the formula

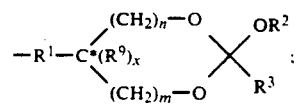

$R^9$ is hydrogen or $C_{1-4}$ primary or secondary alkyl;
m is 0 or 1;
n is from 1 to 2-m; and
x is 0 when $R^2$ and $C^*$ form a ring and is otherwise 1.

By the term "ortho ester" is meant a compound in which one carbon atom is attached to another by a direct carbon-carbon bond, and to three further carbon atoms through oxygen. Such compounds can be considered to be esters of the hypothetical ortho acids R-C(OH)$_3$, wherein R is an organic radical. The existence of such ortho acids is for the most part unknown, since they immediately dehydrate to conventional carboxylic acids. However, esters of such acids are known and the compounds of this invention are esters of this type.

In formula I, $R^1$ is a $C_{1-6}$ alkylene radical such as methylene, ethylene, propylene, trimethylene, pentamethylene or hexamethylene. It is most often methylene.

The $R^2$ radical may be a $C_{1-4}$ primary or secondary alkyl radical such as methyl, ethyl, n-propyl, isopropyl, n-butyl, isobutyl or secondary butyl. Primary radicals and especially the methyl radical are generally preferred.

It is also possible for $R^2$ to form a second 5-or 6-membered ring with other portions of the molecule. For this purpose, one of the carbon atoms in the ortho ester ring is designated $C^*$ to indicate its role as part of said second ring.

The $R^3$ value may be a $C_{1-4}$ primary or secondary alkyl radical as defined above for $R^2$, or a $C_{6-10}$ aromatic (preferably aromatic hydrocarbon) radical. Finally, it is possible for $R^2$ and $R^3$ together to form a 5-, 6- or 7-membered ring with the atoms connecting them. Thus, the invention includes certain spiro ortho ester-capped polyphenylene ethers.

The $R^9$ radical may be hydrogen or an alkyl radical similar to $R^2$ and $R^3$. It is preferably hydrogen.

It is also possible for $R^2$ to form a second 5-or 6-membered ring with other portions of the molecule. For this purpose, one of the carbon atoms in the ortho ester ring is designated $C^*$ to indicate its role as part of said second ring.

The preferred identity of $R^5$ will depend to some extent on the reactivity desired for the capped polyphenylene ether prepared from the ortho ester-subsituted chlorotriazine and the nature of the other polymer with which copolymer formation is desired. Ortho ester groups are substantially more reactive with carboxylic acid groups than with amine groups. Thus, the formation of a copolymer between a capped polyphenylene ether of this invention and the amine group in an amine-terminated polyamide or the like will require the presence of a Lewis acid as catalyst when $R^5$ is itself an ortho ester group or is substantially non-reactive; e.g., when it is an alkyl radical or a hindered aromatic radical such as 2,6-xylyl or mesityl (2,4,6-trimethylphenyl).

When $R^5$ is a relatively unhindered aromatic radical (e.g., phenyl), uncatalyzed displacement thereof by the amine group can take place with the formation of a copolymer. Accordingly, substituted chlorotriazines of the invention in which $R^5$ is phenyl or a similarly unhindered aromatic radical are convertible to capped polyphenylene ethers containing two groups capable of copolymer-forming reactions, one (the ortho ester group) with carboxylic acid groups and the other (the phenyl group) with amine groups.

The values of m and n depend on whether the cyclic ortho ester moiety is a 5-membered or 6-membered ring. In general, 5-membered rings are preferred; that is, m is 0 and n is 1. However, the invention also includes compositions in which a 6-membered ring is present, which requires either that m and n both be 1 or that m be 0 and n be 2.

The value of the subscript x also depends on the cyclic structure of the ortho ester moiety. If C* is part of a ring structure with $R^2$, all four valences thereof are satisfied and x will be 0. If this is not the case, x will be 1.

The following are illustrative ortho ester moieties which may be present in formula I:

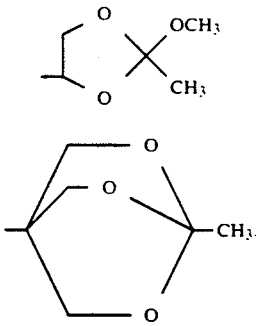

Formula II is the 4-(2-methoxy-2-methyl-1,3-dioxolanyl) radical and is usually preferred. Intermediates for preparation of such compounds include 4-hydroxymethyl- 2-methoxy-2-methyl-1,3-dioxolane, which is obtainable by the reaction of glycerol and methyl orthoacetate. An improved method for the preparation of this and structurally related compounds in substantially pure form and the products thus obtained are disclosed and claimed in copending, commonly owned application Ser. No. 07/623,838. Formula III is the 4-(1-methyl-2,6,7-trioxabicyclo[2.2.2]octyl) radical; the methylol derivative thereof can be prepared by the reaction of ethyl orthoacetate with a substantially equimolar amount of pentaerythritol.

The ortho ester-substituted chlorotriazines of this invention may be prepared by the sequential reaction of a hydroxy compound of the formula $R^5 OH$ and a hydroxysubstituted ortho ester of the formula

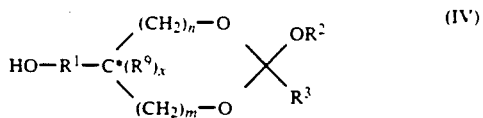

with a chlorotriazine of the formula

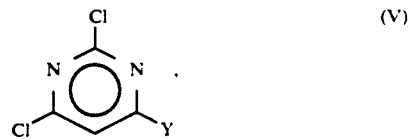

wherein Y is Cl or $OR^5$, in the presence of an alkaline reagent such as sodium hydroxide, potassium hydroxide, pyridine or triethylamine. The reaction may be conducted at temperatures from about $-10°$ to about $25°$ C., preferably about $0°-10°$ C., employing substantially stoichiometric proportions of the reagents. It is frequently convenient to conduct the reaction in a substantially inert organic solvent such as methylene chloride, chloroform, chlorobenzene, toluene or xylene. If that is the case and if the alkaline reagent is an aqueous base such as sodium hydroxide, the employment of a phase transfer catalyst is generally advantageous. Any of such catalysts which are stable and effective under the prevailing reaction conditions may be used; those skilled in the art will readily perceive which ones are suitable. Particularly preferred are the tetraalkylammonium chlorides wherein at least two alkyl groups per molecule, typically two or three, contain about 5–20 carbon atoms.

Following preparation of the ortho ester-substituted chlorotriazine, it may be isolated by conventional means, typically by separation of the organic layer, washing, drying and solvent stripping.

The preparation of the ortho ester-substituted chlorotriazines of this invention is illustrated by the following examples. All percentages in the examples herein are by weight.

EXAMPLE 1

A 1-liter round-bottomed flask equipped with a pressure equalizing addition funnel was flushed with nitrogen and charged with 41.5 grams (451 mmol.) of glycerol, 750 ml. of methylene chloride and 100 mg. of p-toluenesulfonic acid. Methyl orthoacetate, 56.9 grams (473 mmol.), was added over 5 minutes at room temperature, with stirring; stirring was continued for 18 hours after which 1 gram of anhydrous sodium carbonate was added and the mixture was stirred for one additional hour and filtered. The solvent was stripped under vacuum to yield 65 grams (97% of theoretical) of 4-hydroxymethyl-2-methoxy-2-methyl-1,3-dioxolane as a clear oil. Its molecular structure was confirmed by proton and carbon-13 nuclear magnetic resonance spectroscopy.

A 3-necked 500-ml. round-bottomed flask equipped with a magnetic stirrer, pressure equalizing addition funnel and thermometer was charged with 22.63 grams (123 mmol.) of cyanuric chloride, 17.54 grams (128.8 mmol.) of mesitol and 250 ml. of methylene chloride. The flask was cooled to 0° C. and 14.72 grams (184 mmol.) of 50% aqueous sodium hydroxide solution was added dropwise at 0°–5° C., with stirring. The reaction mixture was warmed to room temperature and stirring was continued for 85 minutes, after which the liquid (a solution of the desired mesitoxydichlorotriazine) was decanted from the precipitated solids and the flask was washed and recharged with the decanted liquid.

There was added three drops of a commercially available methyltrialkylammonium chloride in which the alkyl groups contained 8–10 carbon atoms, and the flask was cooled to 0° C. Triethylamine, 0.5 ml., and 20 grams (135 mmol.) of 4-hydroxymethyl-2-methoxy-2-methyl-1,3-dioxolane were added, after which 14.72 grams (184 mmol.) of 50% aqueous sodium hydroxide solution was introduced dropwise, with stirring and cooling to 0°–5° C. The mixture was warmed to room temperature and stirred overnight, after which the organic layer was separated, washed three times with distilled water, dried over anhydrous magnesium sulfate, filtered and vacuum stripped. There was obtained 48 grams (99% of theoretical) of the desired 2-chloro-4-(2-methoxy-2-methyl-1,3-dioxolanyl)methoxy-6-(2,4,6-trimethylphenoxy)-1,3,5-triazine, containing about 15% bis(2,4,6-trimethylphenoxy) chlorocyanurate as an impurity. The molecular structure was confirmed by proton nuclear magnetic resonance spectroscopy.

EXAMPLE 2

The procedure of Example 1 is repeated, substituting 1-methyl-4-hydroxymethyl-2,6,7-trioxabicyclo[2.2.2]octane on an equimolar basis for the substituted dioxolane. The bicyclooctane could be prepared by the reaction of ethyl orthoacetate with an equimolar amount of pentaerythritol. A similar product is obtained.

EXAMPLE 3

The procedure of Example 1 is repeated, substituting phenol on an equimolar basis for the mesitol. The product is the desired 2-chloro-4-(2-methoxy-2-methyl-1,3-dioxolanyl)methoxy-6-phenoxy-1,3,5-triazine.

EXAMPLE 4

A 3-necked 500-ml. round-bottomed flask equipped with a magnetic stirrer, pressure equalizing addition funnel and thermometer was charged with 22.63 grams (123 mmol.) of cyanuric chloride and 250 ml. of methylene chloride. The flask was cooled to 0° C. and 0.5 ml. of 2,6-lutidine, five drops of a commercially available methyltrialkylammonium chloride in which the alkyl groups contained 8–10 carbon atoms and 19.13 grams (129 mmol.) of 4-hydroxymethyl-2-methoxy-2-methyl-1,3-dioxolane were added, followed by dropwise addition of 11.8 grams (148 mmol.) of 50% aqueous sodium hydroxide solution at 0°–10° C., with stirring. Stirring was continued for 1 hour, after which 11.6 grams (123 mmol.) of phenol was added and an additional 11.8 grams of sodium hydroxide solution was introduced dropwise in the same manner.

The flask was warmed to room temperature and stirred overnight, after which 0.5 ml. of triethylamine was added. The organic layer was separated, diluted with further methylene chloride, washed three times with distilled water, dried over anhydrous magnesium sulfate, filtered and vacuum stripped. There was obtained 37 grams (85% of theoretical) of the desired 2-chloro-4-(2-methoxy-2-methyl-1,3-dioxolanyl)methoxy-6-phenoxy-1,3,5-triazine, containing about 27% diphenoxy chlorocyanurate as an impurity. The molecular structure was confirmed by proton nuclear magnetic resonance spectroscopy.

The ortho ester-substituted chlorotriazines of this invention are useful as capping agents for polyphenylene ethers. Capped polyphenylene ethers thus obtained, as well as the method for their preparation, are disclosed and claimed in copending, commonly owned application Ser. No. 07/566,025. The polyphenylene ethers which may be so capped encompass numerous variations and modifications all of which are applicable to the present invention, including but not limited to those described hereinafter.

The polyphenylene ethers comprise a plurality of structural units having the formula

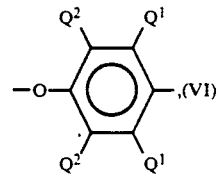

wherein each $Q^1$ is independently halogen, primary or secondary lower alkyl, phenyl, haloalkyl, aminoalkyl, hydrocarbonoxy, or halohydrocarbonoxy wherein at least two carbon atoms separate the halogen and oxygen atoms; and each $Q^2$ is independently hydrogen, halogen, primary or secondary lower alkyl, phenyl, haloalkyl, hydrocarbonoxy or halohydrocarbonoxy as defined for $Q^1$. Examples of primary lower alkyl groups (i.e., alkyl groups having up to 7 carbon atoms) suitable as $Q^1$ and $Q^2$ are methyl, ethyl, n-propyl, n-butyl, isobutyl, n-amyl, isoamyl, 2-methylbutyl, n-hexyl, 2,3-dimethylbutyl, 2-, 3- or 4-methylpentyl and the corresponding heptyl groups. Examples of secondary lower alkyl groups are isopropyl, sec-butyl and 3-pentyl. Preferably, any alkyl radicals are straight chain rather than branched. Most often, each $Q^1$ is alkyl or phenyl, especially $C_{1-4}$ alkyl, and each $Q^2$ is hydrogen. Suitable polyphenylene ethers are disclosed in a large number of patents.

Both homopolymer and copolymer polyphenylene ethers are included. Suitable homopolymers are those containing, for example, 2,6-dimethyl-1,4-phenylene ether units. Suitable copolymers include random copolymers containing such units in combination with (for example) 2,3,6-trimethyl-1,4-phenylene ether units. Many suitable random copolymers, as well as homopolymers, are disclosed in the patent literature.

Also included are polyphenylene ethers containing moieties which modify properties such as molecular weight, melt viscosity and/or impact strength. Such polymers are described in the patent literature and may be prepared by grafting onto the polyphenylene ether in known manner such vinyl monomers as acrylonitrile and vinylaromatic compounds (e.g., styrene), or such polymers as polystyrenes and elastomers. The product typically contains both grafted and ungrafted moieties. Other suitable polymers are the coupled polyphenylene ethers in which the coupling agent is reacted in known manner with the hydroxy groups of two polyphenylene ether chains to produce a higher molecular weight polymer containing the reaction product of the hydroxy groups and the coupling agent, provided substantial proportions of free hydroxy groups remain present. Illustrative coupling agents are low molecular weight polycarbonates, quinones, heterocycles and formals.

The polyphenylene ether generally has a number average molecular weight within the range of about 3,000–40,000 and a weight average molecular weight within the range of about 20,000–80,000, as determined by gel permeation chromatography. Its intrinsic viscosity is most often in the range of about 0.15–0.6 dl./g., as measured in chloroform at 25° C.

The polyphenylene ethers are typically prepared by the oxidative coupling of at least one corresponding monohydroxyaromatic compound. Particularly useful and readily available monohydroxyaromatic compounds are 2,6-xylenol (wherein each $Q^1$ is methyl and each $Q^2$ is hydrogen), whereupon the polymer may be characterized as a poly(2,6-dimethyl-1,4-phenylene ether), and 2,3,6-trimethylphenol (wherein each $Q^1$ and one $Q^2$ is methyl and the other $Q^2$ is hydrogen).

A variety of catalyst systems are known for the preparation of polyphenylene ethers by oxidative coupling. There is no particular limitation as to catalyst choice and any of the known catalysts can be used. For the most part, they contain at least one heavy metal compound such as a copper, manganese or cobalt compound, usually in combination with various other materials.

A first class of preferred catalyst systems consists of those containing a copper compound. Such catalysts are disclosed, for example, in U.S. Pat. Nos. 3,306,874, 3,306,875, 3,914,266 and 4,028,341. They are usually combinations of cuprous or cupric ions, halide (i.e., chloride, bromide or iodide) ions and at least one amine.

Catalyst systems containing manganese compounds constitute a second preferred class. They are generally alkaline systems in which divalent manganese is combined with such anions as halide, alkoxide or phenoxide. Most often, the manganese is present as a complex with one or more complexing and/or chelating agents such as dialkylamines, alkanolamines, alkylenediamines, o-hydroxyaromatic aldehydes, o-hydroxyazo compounds, ω-hydroxyoximes (monomeric and polymeric), o-hydroxyaryl oximes and β-diketones. Also useful are known cobalt-containing catalyst systems. Suitable manganese and cobalt-containing catalyst systems for polyphenylene ether preparation are known in the art by reason of disclosure in numerous patents and publications.

The polyphenylene ethers which may be employed for the purposes of this invention include those which comprise molecules having at least one of the end groups of the formulas

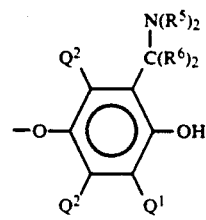

and

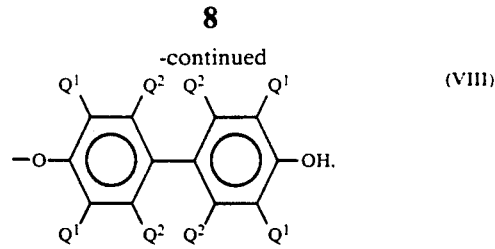

wherein $Q^1$ and $Q^2$ are as previously defined; each $R^5$ is independently hydrogen or a $C_{1-6}$ primary alkyl radical; and each $R^6$ is independently hydrogen or alkyl, with the proviso that the total number of carbon atoms in both $R^6$ radicals is 6 or less. Preferably, each $R^5$ is alkyl, especially methyl or n-butyl, and each $R^6$ is hydrogen.

Polymers containing the aminoalkyl-substituted end groups of formula VII are typically obtained by incorporating an appropriate primary or secondary monoamine as one of the constituents of the oxidative coupling reaction mixture, especially when a copper- or manganese-containing catalyst is used. Such amines, especially the dialkylamines and preferably di-n-butylamine and dimethylamine, frequently become chemically bound to the polyphenylene ether, most often by replacing one of the α-hydrogen atoms on one or more $Q^1$ radicals. The principal site of reaction is the $Q^1$ radical adjacent to the hydroxy group on the terminal unit of the polymer chain. During further processing and/or blending, the aminoalkyl-substituted end groups may undergo various reactions, probably involving a quinone methide-type intermediate of the formula

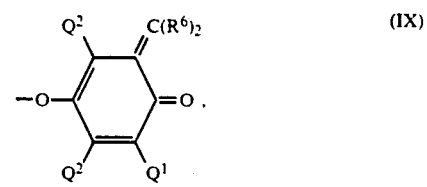

with numerous beneficial effects often including an increase in impact strength and compatibilization with other blend components. Reference is made to U.S. Pat. Nos. 4,054,553, 4,092,294, 4,477,649, 4,477,651 and 4,517,341, the disclosures of which are incorporated by reference herein.

Polymers with 4-hydroxybiphenyl end groups of formula VIII are often especially useful in the present invention. They are typically obtained from reaction mixtures in which a by-product diphenoquinone of the formula

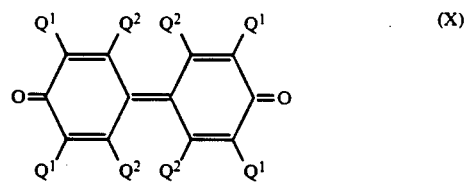

is present, especially in a copper-halide-secondary or tertiary amine system. In this regard, the disclosure of U.S. Pat. No. 4,477,649 is again pertinent as are those of U.S. Pat. No. 4,234,706 and 4,482,697, which are also incorporated by reference herein. In mixtures of this type, the diphenoquinone is ultimately incorporated into the polymer in substantial proportions, largely as an end group.

In many polyphenylene ethers obtained under the above-described conditions, a substantial proportion of the polymer molecules, typically constituting as much as about 90% by weight of the polymer, contain end groups having one or frequently both of formulas VII and VIII. It should be understood, however, that other end groups may be present and that the invention in its broadest sense may not be dependent on the molecular structures of the polyphenylene ether end groups.

The use of polyphenylene ethers containing substantial amounts of unneutralized amino nitrogen may afford compositions with undesirably low impact strengths. The amino compounds include, in addition to the aforementioned aminoalkyl end groups, traces of amine (particularly secondary amine) in the catalyst used to form the polyphenylene ether.

The present invention therefore includes the use of polyphenylene ethers in which a substantial proportion of amino compounds has been removed or inactivated. Polymers so treated contain unneutralized amino nitrogen, if any, in amounts no greater than 800 ppm. and more preferably in the range of about 100-800 ppm.

A preferred method of inactivation is by extrusion of the polyphenylene ether at a temperature within the range of about 230°-350° C., with vacuum venting. This is preferably achieved in a preliminary extrusion step, by connecting the vent of the extruder to a vacuum pump capable of reducing the pressure to about 200 torr or less.

It is believed that this inactivation method aids in the removal by evaporation of any traces of free amines (predominantly secondary amines) in the polymer, including amines generated by conversion of aminoalkyl end groups to quinone methides of the type represented by formula IX.

It will be apparent to those skilled, in the art from the foregoing that the polyphenylene ethers contemplated for use include all those presently known, irrespective of variations in structural units or ancillary chemical features.

The reaction between the polyphenylene ether and the ortho ester-substituted chlorotriazine may be conducted at temperatures from about $-10°$ to about $100°$ C. in the presence of an alkaline reagent such as sodium hydroxide, most often in the form of an aqueous solution. It is frequently preferred to employ a relatively non-polar solvent and phase transfer catalyst of the type previously described.

The proportions of ortho ester and polyphenylene ether may be varied widely, depending upon the proportion of copolymer desired in the blend to be compatibilized. Molar ratios of ortho ester to polyphenylene ether, the latter in terms of non-hydrogen bonded hydroxy end groups, are typically in the range of about 0.1-3.0:1. The molar ratio of base to polyphenylene ether is usually in the range of about 1-2:1, and the phase transfer catalyst (when employed) is present in a minor amount effective to catalyze the reaction, such amounts being known in the art as readily determinable by simple experimentation.

Following completion of the capping reaction, the reaction mixture can be worked up by conventional operations, typically including neutralization of remaining alkaline reagent with a suitable weakly acidic material which is compatible with the ortho ester group, such as carbon dioxide, and precipitation of the product from solution by addition of a non-solvent. Among the non-solvents which may be employed are methanol, 1-propanol, acetone, acetonitrile and mixtures thereof. It is also possible to employ the solution of the capped polyphenylene ether directly in copolymer formation, as by a reactive extrusion process leading to removal of the solvent by volatilization or accompanied by addition of an anti-solvent and isolation of a slurry as the extrudate.

The preparation of capped polyphenylene ethers from the ortho ester-substituted chlorotriazines of this invention is illustrated by the following examples. In each example, the polyphenylene ether employed was a commercially available poly(2,6-dimethyl-1,4-phenylene ether) having an intrinsic viscosity in chloroform at 25° C. of 0.40 dl./g. Molar proportions of polyphenylene ether are in terms of non-hydrogen bonded hydroxy end groups.

EXAMPLE 5

A 3-necked 12-liter flask equipped with a paddle stirrer, thermometer and nitrogen inlet was charged with a solution of 1100 grams (64.7 mmol.) of polyphenylene ether in 5.5 liters of toluene. There was added 4.1 grams of the methyltrialkylammonium chloride of Example 1 and 7.77 grams (97 mmol.) of 50% aqueous sodium hydroxide solution. The mixture was stirred vigorously for 15 minutes, whereupon 48.5 grams (122.6 mmol.) of the product of Example 1 was added. Stirring was continued for 35 minutes, after which remaining base was neutralized by bubbling gaseous carbon dioxide through the solution for 7 minutes. The solution was poured into an excess of methanol and the polymer which precipitated was dried at 110° C. in vacuum. There was obtained 1096 grams of the desired ortho ester-capped polyphenylene ether. Its structure was confirmed by proton nuclear magnetic resonance and Fourier transform infrared spectroscopy.

EXAMPLE 6

The procedure of Example 5 is repeated, substituting the product of Example 2 on an equimolar basis for that of Example 1. A similar capped polymer is obtained.

EXAMPLE 7

The procedure of Example 5 is repeated, substituting the product of Example 3 on an equimolar basis for that of Example 1. A similar capped polymer is obtained.

EXAMPLE 8

A 3-necked 5-liter flask equipped with a paddle stirrer, thermometer and nitrogen inlet was charged with a solution of 550 grams (32.4 mmol.) of polyphenylene ether in 3 liters of toluene. There was added 5.5 grams of the methyltrialkylammonium chloride of Example 1 and 3.88 grams (48.5 mmol.) of 50% aqueous sodium hydroxide solution. The mixture was stirred vigorously for 30 minutes, whereupon a solution of 25 grams (70.7 mmol.) of the product of Example 4 in 100 ml. of methylene chloride was added. Stirring was continued for 30 minutes, after which remaining base was neutralized by bubbling gaseous carbon dioxide through the solution for 10 minutes. The solution was poured into an excess of methanol and the polymer which precipitated was dried at 110° C. in vacuum. The product was the desired ortho ester-capped polyphenylene ether. Its structure was confirmed by proton nuclear magnetic resonance and Fourier transform infrared spectroscopy.

The ortho ester-capped polyphenylene ethers react with other polymers containing reactive groups, particularly those capable of nucleophilic aliphatic substitution such as amine, hydroxy, thio and carboxy groups and functional derivatives thereof, to form copolymer-containing compositions. Compositions of this type in which the other polymer contains carboxylic acid groups are also disclosed and claimed in the aforementioned application Ser. No. 07/566,025. Compositions comprising copolymers with amine group-containing polymers are disclosed and claimed in copending, commonly owned application Ser. No. 07/727,209.

The carboxylic acid groups may be present at any location in the other polymer molecule; i.e., they may be end groups, substituents or grafted moieties. Thus, it is possible to form copolymer-containing compositions from numerous polymers which are otherwise incompatible with polyphenylene ethers, including polyesters and carboxy-functionalized olefin polymers. By reason of the presence of the copolymer, the copolymer-containing compositions are compatible and may be molded into articles having excellent physical properties. They are also useful for further compatibilizing blends of the two polymers to form molding compositions having similar excellent properties.

Polyesters suitable for preparing the copolymer-containing compositions of this invention include those comprising structural units of the formula

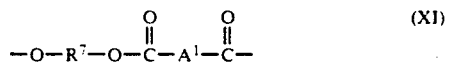

wherein each $R^7$ is independently a divalent aliphatic, alicyclic or aromatic hydrocarbon or polyoxyalkylene radical and $A^1$ is a divalent aromatic radical. Such polyesters include thermoplastic polyesters illustrated by poly(alkylene dicarboxylates), elastomeric polyesters, polyarylates, and polyester copolymers such as copolyestercarbonates. Because the principal reaction which occurs with the ortho ester groups in the capped polyphenylene ether involves a carboxylic acid group of the polyester, it is highly preferred that said polyester have a relatively high carboxylic end group concentration. Concentrations in the range of about 5-250 microequivalents per gram are generally suitable, with 10-100 microequivalents per gram being preferable, 30-100 being more preferable and 40-80 being particularly desirable.

The polyester may include structural units of the formula

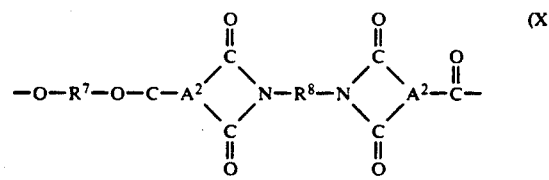

wherein $R^7$ is as previously defined, $R^8$ is a polyoxyalkylene radical and $A^2$ is a trivalent aromatic radical. The $A^1$ radical in formula XI is most often p- or m-phenylene or a mixture thereof, and $A^2$ in formula XII is usually derived from trimellitic acid and has the structure

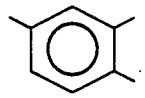

The $R^7$ radical may be, for example, a $C_{2-10}$ alkylene radical, a $C_{6-10}$ alicyclic radical, a $C_{6-20}$ aromatic radical or a polyoxyalkylene radical in which the alkylene groups contain about 2-6 and most often 4 carbon atoms. As previously noted, this class of polyesters includes the poly(alkylene terephthalates) and the polyarylates. Poly(alkylene terephthalates) are frequently preferred, with poly(ethylene terephthalate) and poly(butylene terephthalate) being most preferred.

The polyester generally has a number average molecular weight in the range of about 20,000–70,000, as determined by intrinsic viscosity (IV) at 30° C. in a mixture of 60% (by weight) phenol and 40% 1,1,2,2-tetrachloroethane.

The olefin polymers (hereinafter sometimes designated "polyolefins") which may be functionalized for use in the preparation of copolymer-containing compositions are homopolymers and copolymers of known aliphatic olefins including ethylene, propylene, 1-butene, 2-butene, 1-pentene, 2-pentene, 2-methyl-1-pentene, 3-methyl-1-pentene, 1-octene and 1-dodecene. The $C_{2-6}$ olefins are preferred, with ethylene and propylene being most preferred.

For copolymer formation, it is essential for the polyolefin to have the aforementioned carboxylic acid substituents. They may be incorporated in the polyolefin by employing suitable functional comonomers, such as acrylic acid or maleic anhydride, in the formation thereof. They may also be provided by graft polymerization on an already prepared polyolefin, using the same monomers, or by other art-recognized means of functionalization. Any of the commercially available graft-functionalized polyolefins may be used, or suitable polymers may be prepared from commercially available unfunctionalized polyolefins such as low density polyethylene, high density polyethylene and polypropylene.

It is highly preferred to employ a blending method which results in the formation of an intimate blend for the preparation of copolymer-containing compositions. Suitable methods include solution blending, although such procedures are of limited applicability to many polymers (especially polyesters) by reason of their insolubility in most common solvents. For this reason and because of the availability of melt blending equipment in commercial polymer processing facilities, melt reaction procedures are generally preferred. Conventional melt blending procedures and equipment may be employed, with extrusion often preferred because of its relative convenience and particular suitability. Typical reaction temperatures are in the range of about 175°–350° C. It is usually preferred to extrude with vacuum venting as described hereinabove with reference to uncapped polyphenylene ether, particularly if vacuum venting was not previously employed in the preparation or processing of said polyphenylene ether.

Those skilled in the art will be familiar with blending methods and apparatus capable of intimately blending resinous constituents, especially by kneading. They are exemplified by disc-pack processors and various types of extrusion equipment. Illustrations of the latter are continuous mixers; single screw kneading extruders;

corotating, intermeshing and counterrotating, non-intermeshing twin screw extruders having such features as staggered configuration screws, forward-flighted compounders, cylindrical bushings and left-handed screw elements; and extruders having screws which include at least one and preferably two kneading block elements.

In addition to copolymer, the copolymer-containing compositions may also contain unreacted polyphenylene ether. This will include any polyphenylene ether molecules having only hydrogen bonded end groups, as well as other polyphenylene ether which is unfunctionalized as a result of incomplete capping, which is functionalized but fails to react with polyester or which is introduced in unfunctionalized form. In any event, molded parts produced from said compositions are generally ductile and have higher impact strengths than those produced from simple blends, which are incompatible and often exhibit brittleness or delamination as previously described.

It is also contemplated to include in the blending step impact modifiers compatible with either or both of the polyphenylene ether and the other polymer.

Impact modifiers for polyphenylene ether compositions are well known in the art. They are most often elastomeric polymers, typically derived from one or more monomers selected from the group consisting of olefins, vinyl aromatic monomers, acrylic and alkylacrylic acids and their ester derivatives as well as conjugated dienes. Especially preferred impact modifiers are the rubbery high molecular weight materials including natural and synthetic polymeric materials showing elasticity at room temperature. They include both homopolymers and copolymers, including random, block, radial block, graft and core-shell copolymers as well as combinations thereof.

Polyolefins or olefin-based copolymers include low density polyethylene, high density polyethylene, linear low density polyethylene, isotactic polypropylene, poly(1-butene), poly(4-methyl-1-pentene), propylene-ethylene copolymers and the like. Additional olefin copolymers include copolymers of one or more α-olefins, particularly ethylene, with copolymerizable monomers including, for example, vinyl acetate, acrylic acid and alkylacrylic acids as well as the ester derivatives thereof including, for example, ethyl acrylate, methyl methacrylate and the like. Also suitable are the ionomer resins, which may be wholly or partially neutralized with metal ions.

A particularly useful class of impact modifiers are those derived from the vinyl aromatic monomers. These include AB and ABA type block and radial block copolymers and vinyl aromatic conjugated diene core-shell graft copolymers.

An especially preferred subclass of vinyl aromatic monomer-derived resins is the block copolymers comprising monoalkenyl arene (usually styrene) blocks and conjugated diene (e.g., butadiene or isoprene) or olefin (e.g., ethylene-propylene, ethylene-butylene) blocks and represented as AB and ABA block copolymers. The conjugated diene blocks may be partially or entirely hydrogenated, whereupon the properties are similar to the olefin block copolymers.

Suitable AB type block copolymers are disclosed in, for example, U.S. Pat. Nos. 3,078,254; 3,402,159; 3,297,793; 3,265,765 and 3,594,452 and UK Patent 1,264,741, all incorporated herein by reference. Exemplary of typical species of AB block copolymers are polystyrene-polybutadiene (SBR), polystyrene-polyisoprene and poly(alphamethylstyrene)-polybutadiene. Such AB block copolymers are available commercially from a number of sources, including Phillips Petroleum under the tradename SOLPRENE.

Additionally, ABA triblock copolymers and processes for their production as well as hydrogenation, if desired, are disclosed in U.S. Pat. Nos. 3,149,182; 3,231,635; 3,462,162; 3,287,333; 3,595,942; 3,694,523 and 3,842,029, all incorporated herein by reference.

Examples of triblock copolymers include polystyrene-polybutadiene-polystyrene (SBS), polystyrenepolyisoprene-polystyrene (SIS), poly(α-methylstyrene)polybutadiene-poly(α-methylstyrene) and poly(α-methylstyrene)-polyisoprene-poly(α-methylstyrene). Particularly preferred triblock copolymers are available commercially as CARIFLEX®, KRATON D® and KRATON G® from Shell.

Another class of impact modifiers is derived from conjugated dienes. While many copolymers containing conjugated dienes have been discussed above, additional conjugated diene modifier resins include, for example, homopolymers and copolymers of one or more conjugated dienes including, for example, polybutadiene, butadiene-styrene copolymers, isoprene-isobutylene copolymers, chlorobutadiene polymers, butadiene-acrylonitrile copolymers, polyisoprene, and the like. Ethylene-propylene-diene monomer rubbers may also be used. These EPDM's are typified as comprising predominantly ethylene units, a moderate amount of propylene units and up to about 20 mole percent of non-conjugated diene monomer units. Many such EPDM's and processes for the production thereof are disclosed in U.S. Pat. Nos. 2,933,480; 3,000,866; 3,407,158; 3,093,621 and 3,379,701, incorporated herein by reference.

Other suitable impact modifiers are the core-shell type graft copolymers. In general, these have a predominantly conjugated diene rubbery core or a predominantly crosslinked acrylate rubbery core and one or more shells polymerized thereon and derived from monoalkenylarene and/or acrylic monomers alone or, preferably, in combination with other vinyl monomers. Such core-shell copolymers are widely available commercially, for example, from Rohm and Haas Company under the trade names KM-611, KM-653, KM-330, and are described in U.S. Pat. Nos. 3,808,180; 4,034;013; 4,096,202; 4,180,494 and 4,292,233.

Also useful are the core-shell copolymers wherein an interpenetrating network of the resins employed characterizes the interface between the core and shell. Especially preferred in this regard are the ASA type copolymers available from General Electric Company and sold as GELOY ™ resin and described in U.S. Pat. No. 3,944,631.

In addition, there may be employed the abovedescribed polymers and copolymers having copolymerized therewith or grafted thereon monomers having functional groups and/or polar or active groups. Finally, other suitable impact modifiers include Thiokol rubber, polysulfide rubber, polyurethane rubber, polyether rubber (e.g., polypropylene oxide), epichlorohydrin rubber, ethylene-propylene rubber, thermoplastic polyester elastomers and thermoplastic ether-ester elastomers.

There may also be present in the copolymer-containing compositions conventional ingredients such as fillers, flame retardants, pigments, dyes, stabilizers, antistatic agents, crystallization aids, mold release agents and the like, as well as resinous components not previously discussed.

The proportions of polyphenylene ether, other polymer and other resinous materials such as impact modifier (if present) are not critical; they may be widely varied to provide compositions having the desired properties. Most often, the polyphenylene ether is employed in an amount in the range of about 5-95%, preferably about 15-50%, of the composition by weight. Impact modifiers such as diblock or triblock copolymers are usually present in an amount up to about 25 parts per 100 parts of polyphenylene ether.

The preparation of copolymer-containing compositions from polyphenylene ethers capped with the ortho ester-substituted chlorotriazines of this invention is illustrated by the following examples. All percentages are by weight.

EXAMPLES 9-11

Dry blends of the product of Example 5, uncapped polyphenylene ether (in Example 11), a commercially available poly(butylene terephthalate) having a number average molecular weight of about 50,000 as determined by gel permeation chromatography, and a commercially available triblock copolymer with polystyrene end blocks having weight average molecular weights of 29,000 and a hydrogenated butadiene midblock having a weight average molecular weight of 116,000 were prepared and extruded at temperatures in the range of 120°-288° C., with vacuum venting. The extrudates were the desired copolymer-containing compositions; they were pelletized, dried for 4 hours at 110° C. and molded into test specimens which were equilibrated for 24 hours at 50% humidity and tested for notched Izod impact strength (ASTM procedure D256). The results are given in the following table.

|  | Example | | |
| --- | --- | --- | --- |
|  | 9 | 10 | 11 |
| Product of Example 5, % | 20 | 36 | 10 |
| Uncapped polyphenylene ether, % | — | — | 10 |
| Poly(butylene terephthalate), % | 70 | 54 | 70 |
| Triblock copolymer, % | 10 | 10 | 10 |
| Impact strength, joules/m. | 684 | 374 | 502 |

EXAMPLE 12

A composition was prepared substantially by the procedure of Examples 9-11, from 30% of the product of Example 8, 60% poly(butylene terephthalate) and 10% triblock copolymer. It was found to have an impact strength of 630 joules/m.

What is claimed is:

1. An ortho ester-substituted chlorotriazine of the formula

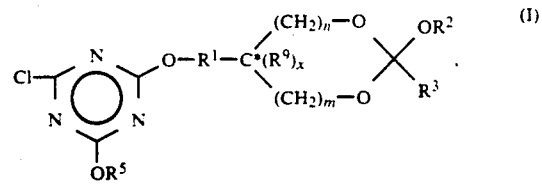

$R^1$ is a $C_{1-6}$ alkylene radical;
$R^2$ is $C_{1-4}$ primary or secondary alkyl radical, or is an alkylene radical forming a 5- or 6-membered ring with C*, and $R^3$ is $C_{1-4}$ primary or secondary alkyl or $C_{6-10}$ aromatic radical, or $R^2$ and $R^3$ together with the atoms connecting them form a 5-, 6- or 7-membered ring;
$R^5$ is an alkyl, cycloalkyl or aromatic radical or a radical of the formula

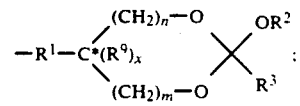

$R^9$ is hydrogen or $C_{1-4}$ primary or secondary alkyl;
m is 0 or 1;
n is from 1 to 2-m; and
x is 0 when $R^2$ and C* form a ring and is otherwise 1.

2. A substituted chlorotriazine according to claim 1 wherein $R^1$ is methylene and $R^9$ is hydrogen 3. A substituted chlorotriazine according to claim 2 wherein $R^3$ is methyl.

4. A substituted chlorotriazine according to claim 3 wherein $R^2$ is methyl.

5. A substituted chlorotriazine according to claim 4 wherein m is 0 and n is 1.

6. A substituted chlorotriazine according to claim 3 wherein $R^2$ is methylene and forms a ring with C*.

7. A substituted chlorotriazine according to claim 3 wherein $R^5$ is an alkyl radical or a 2,6-xylyl or mesityl radical.

8. A substituted chlorotriazine according to claim 7 wherein $R^2$ is methyl.

9. A substituted chlorotriazine according to claim 8 wherein m is 0 and n is 1.

10. A substituted chlorotriazine according to claim 7 wherein $R^2$ is methylene and forms a ring with C*.

11. A substituted chlorotriazine according to claim 3 wherein $R^5$ is phenyl.

12. A substituted chlorotriazine according to claim 11 wherein $R^2$ is methyl.

13. A substituted chlorotriazine according to claim 12 wherein m is 0 and n is 1.

14. A substituted chlorotriazine according to claim 11 wherein $R^2$ is methylene and forms a ring with C*.

* * * * *

UNITED STATES PATENT AND TRADEMARK OFFICE
CERTIFICATE OF CORRECTION

PATENT NO. : 5,142,049

DATED : August 25, 1992

INVENTOR(S) : Farid F. Khouri et al.

It is certified that error appears in the above-identified patent and that said Letters Patent is hereby corrected as shown below:

Column 2, lines 9 and 19, "$R^5$" should read --$R^4$--. Column 3, lines 1, 11, 15 and 19, "$R^5$" should read --$R^4$--. Column 4, lines 1 and 18, "$R^5$" should read --$R^4$--; line 15, the formula should be — 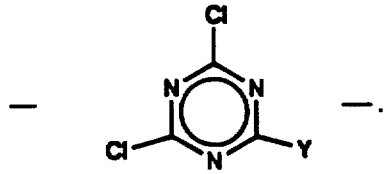 —.

Column 16, lines 10, 19, 42 and 51, "$R^5$" should read --$R^4$--.

Signed and Sealed this

Twenty-eighth Day of September, 1993

*Attest:*

BRUCE LEHMAN

*Attesting Officer*     Commissioner of Patents and Trademarks